(12) United States Patent
Park (10) Patent No.: US 12,375,745 B2
(45) Date of Patent: Jul. 29, 2025

(54) CONTENT DISTRIBUTION SYSTEM AND METHOD

(71) Applicant: SURGIYO LLC, Lathrop, CA (US)

(72) Inventor: Stanley Seung Kwan Park, Lathrop, CA (US)

(73) Assignee: SURGIYO LLC, Lathrop, CA (US)

( * ) Notice: Subject to any disclaimer, the term of this patent is extended or adjusted under 35 U.S.C. 154(b) by 0 days.

(21) Appl. No.: 17/938,461

(22) Filed: Oct. 6, 2022

(65) Prior Publication Data
US 2023/0108183 A1  Apr. 6, 2023

Related U.S. Application Data

(60) Provisional application No. 63/337,305, filed on May 2, 2022, provisional application No. 63/253,081, filed on Oct. 6, 2021.

(51) Int. Cl.
| | |
|---|---|
| *H04N 21/2743* | (2011.01) |
| *G11B 27/036* | (2006.01) |
| *G11B 27/06* | (2006.01) |
| *G16H 30/40* | (2018.01) |
| *H04N 21/231* | (2011.01) |

(52) U.S. Cl.
CPC ....... *H04N 21/2743* (2013.01); *G11B 27/036* (2013.01); *G11B 27/06* (2013.01); *G16H 30/40* (2018.01); *H04N 21/231* (2013.01)

(58) Field of Classification Search
CPC .. H04N 21/2743; H04N 21/231; G16H 30/40; G11B 27/036; G11B 27/06
See application file for complete search history.

(56) References Cited

U.S. PATENT DOCUMENTS

| | | |
|---|---|---|
| 2005/0215867 A1 | 9/2005 | Grigsby et al. |
| 2008/0059224 A1 | 3/2008 | Schechter |
| 2010/0100392 A1 | 4/2010 | Rothman et al. |
| 2012/0044250 A1 | 2/2012 | Landers et al. |
| 2012/0216297 A1 | 8/2012 | Cohen et al. |
| 2013/0311207 A1 | 11/2013 | Kemp et al. |
| 2015/0035959 A1* | 2/2015 | Amble ................ A61B 5/0077 348/74 |
| 2015/0117839 A1 | 4/2015 | Oberbrunner et al. |
| 2016/0247537 A1 | 8/2016 | Ricciardi |
| 2017/0294212 A1 | 10/2017 | Allen et al. |
| 2018/0122422 A1 | 5/2018 | Allison et al. |
| 2020/0273581 A1* | 8/2020 | Wolf ...................... G16H 40/63 |

(Continued)

OTHER PUBLICATIONS

International Search Report and Written Opinion in related Application Serial No. PCT/US2022/077686 on Jan. 17, 2023.

(Continued)

*Primary Examiner* — Thai Q Tran
*Assistant Examiner* — Jose M Mesa
(74) *Attorney, Agent, or Firm* — Brian J. Colandreo; Jeffrey T. Placker; Holland & Knight LLP (57) ABSTRACT

A computer-implemented method, computer program product and computing system for enabling a user to select raw procedure content for processing; enabling the user to select one or more sub-portions of the raw procedure content for inclusion within processed procedure content; and processing the one or more sub-portions of the raw procedure content to generate the processed procedure content.

27 Claims, 4 Drawing Sheets

(56) References Cited

U.S. PATENT DOCUMENTS

2022/0141508 A1  5/2022  Schultz et al.
2022/0167057 A1  5/2022  Panje

OTHER PUBLICATIONS

International Search Report and Written Opinion in related Application Serial No. PCT/US2022/077687 on Jan. 17, 2023.
Non-Final Office Action issued in related U.S. Appl. No. 17/938,456 on issue Date; Dec. 1, 2023.
Final Office Action issued in related U.S. Appl. No. 17/938,456 on May 15, 2024.
Non Final Office Action issued in related U.S. Appl. No. 17/938,456 on Oct. 1, 2024.
Final Office Action issued in related U.S. Appl. No. 17/938,456 on May 9, 2025.

* cited by examiner

CONTENT DISTRIBUTION SYSTEM AND METHOD

RELATED APPLICATION(S)

This application claims the benefit of U.S. Provisional Application Nos. 63/253,081 filed on 6 Oct. 2021 and U.S. Provisional Application Nos. 63/337,305 filed on 2 May 2022, the entire contents of which are incorporated herein by reference.

TECHNICAL FIELD

This disclosure relates to video distribution systems and methods and, more particularly, to video distribution systems and methods that enable the simple distribution of surgical videos.

BACKGROUND

In the days of social media, it is generally accepted that everything is available online and everyone has the ability to publish not only their thoughts but also their personal content. Between Facebook™, YouTube™, TikTok™, Twitch™, Twitter™ and Instagram™, the average person now has a platform for the generation and distribution of content. Further, certain people have taken the distribution of such content to new levels, with terms like "influencer" being bestowed upon those individuals that distribute high quantities of content and have large social media followings.

Unfortunately, not all segments of the population are equally skilled concerning the use of social media and the distribution of content, with younger and/or more technical individuals being more skilled in this area than those who are older/less technical.

SUMMARY OF DISCLOSURE

Video Editor

In one implementation, a computer-implemented method is executed on a computing device and includes: enabling a user to select raw procedure content for processing; enabling the user to select one or more sub-portions of the raw procedure content for inclusion within processed procedure content; and processing the one or more sub-portions of the raw procedure content to generate the processed procedure content.

One or more of the following features may be included. The raw procedure content may include video-based raw procedure content. The raw procedure content may concern a medical procedure. The raw procedure content may be stored at a non-public storage location within a remote storage platform. The remote storage platform may include a cloud-based remote storage platform. Enabling the user to select one or more sub-portions of the raw procedure content for inclusion in processed procedure content may include: selecting one or more sub-portions of the raw procedure content to shorten the overall length of the raw procedure content. Enabling the user to select one or more sub-portions of the raw procedure content for inclusion in processed procedure content may include: selecting one or more sub-portions of the raw procedure content to remove one or more undesired portions of the raw procedure content. Processing the one or more sub-portions of the raw procedure content to generate the processed procedure content may include: joining the one or more sub-portions of the raw procedure content to generate the processed procedure content. Processing the one or more sub-portions of the raw procedure content to generate the processed procedure content may include: adding overlay material to the one or more sub-portions of the raw procedure content. Adding overlay material to the one or more sub-portions of the raw procedure content may include one or more of: adding text-based overlay material to the one or more sub-portions of the raw procedure content; adding image/video-based overlay material to the one or more sub-portions of the raw procedure content; and adding voice-based overlay material to the one or more sub-portions of the raw procedure content.

In another implementation, a computer program product resides on a computer readable medium and has a plurality of instructions stored on it. When executed by a processor, the instructions cause the processor to perform operations including enabling a user to select raw procedure content for processing; enabling the user to select one or more sub-portions of the raw procedure content for inclusion within processed procedure content; and processing the one or more sub-portions of the raw procedure content to generate the processed procedure content.

One or more of the following features may be included. The raw procedure content may include video-based raw procedure content. The raw procedure content may concern a medical procedure. The raw procedure content may be stored at a non-public storage location within a remote storage platform. The remote storage platform may include a cloud-based remote storage platform. Enabling the user to select one or more sub-portions of the raw procedure content for inclusion in processed procedure content may include: selecting one or more sub-portions of the raw procedure content to shorten the overall length of the raw procedure content. Enabling the user to select one or more sub-portions of the raw procedure content for inclusion in processed procedure content may include: selecting one or more sub-portions of the raw procedure content to remove one or more undesired portions of the raw procedure content. Processing the one or more sub-portions of the raw procedure content to generate the processed procedure content may include: joining the one or more sub-portions of the raw procedure content to generate the processed procedure content. Processing the one or more sub-portions of the raw procedure content to generate the processed procedure content may include: adding overlay material to the one or more sub-portions of the raw procedure content. Adding overlay material to the one or more sub-portions of the raw procedure content may include one or more of: adding text-based overlay material to the one or more sub-portions of the raw procedure content; adding image/video-based overlay material to the one or more sub-portions of the raw procedure content; and adding voice-based overlay material to the one or more sub-portions of the raw procedure content.

In another implementation, a computing system includes a processor and a memory system configured to perform operations including enabling a user to select raw procedure content for processing; enabling the user to select one or more sub-portions of the raw procedure content for inclusion within processed procedure content; and processing the one or more sub-portions of the raw procedure content to generate the processed procedure content.

One or more of the following features may be included. The raw procedure content may include video-based raw procedure content. The raw procedure content may concern a medical procedure. The raw procedure content may be stored at a non-public storage location within a remote storage platform. The remote storage platform may include a cloud-based remote storage platform. Enabling the user to select one or more sub-portions of the raw procedure content for inclusion in processed procedure content may include: selecting one or more sub-portions of the raw procedure content to shorten the overall length of the raw procedure content. Enabling the user to select one or more sub-portions of the raw procedure content for inclusion in processed procedure content may include: selecting one or more sub-portions of the raw procedure content to remove one or more undesired portions of the raw procedure content. Processing the one or more sub-portions of the raw procedure content to generate the processed procedure content may include: joining the one or more sub-portions of the raw procedure content to generate the processed procedure content. Processing the one or more sub-portions of the raw procedure content to generate the processed procedure content may include: adding overlay material to the one or more sub-portions of the raw procedure content. Adding overlay material to the one or more sub-portions of the raw procedure content may include one or more of: adding text-based overlay material to the one or more sub-portions of the raw procedure content; adding image/video-based overlay material to the one or more sub-portions of the raw procedure content; and adding voice-based overlay material to the one or more sub-portions of the raw procedure content.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
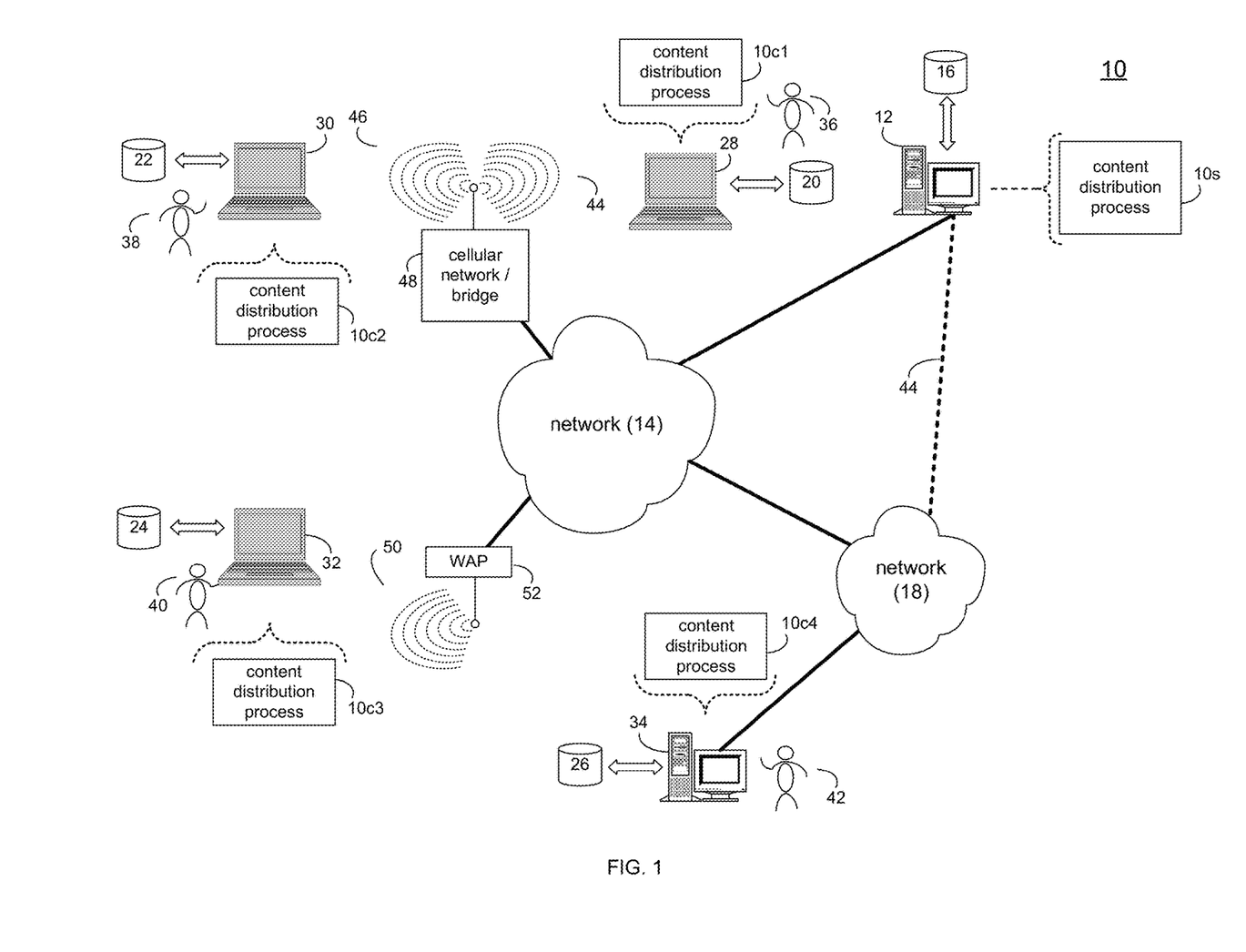
FIG. 1 is a diagrammatic view of a distributed computing network including a computing device that executes a content distribution process according to an embodiment of the present disclosure.

Referring to FIG. 1, there is shown content distribution process 10. Content distribution process 10 may be implemented as a server-side process, a client-side process, or a hybrid server-side/client-side process. For example, content distribution process 10 may be implemented as a purely server-side process via content distribution process 10s. Alternatively, content distribution process 10 may be implemented as a purely client-side process via one or more of content distribution process 10c1, content distribution process 10c2, content distribution process 10c3, and content distribution process 10c4. Alternatively still, content distribution process 10 may be implemented as a hybrid server-side/client-side process via content distribution process 10s in combination with one or more of content distribution process 10c1, content distribution process 10c2, content distribution process 10c3, and content distribution process 10c4. Accordingly, content distribution process 10 as used in this disclosure may include any combination of content distribution process 10s, content distribution process 10c1, content distribution process 10c2, content distribution process 10c3, and content distribution process 10c4.

Content distribution process 10s may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, a smartphone, or a cloud-based computing platform.

The instruction sets and subroutines of content distribution process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of content distribution processes 10c1, 10c2, 10c3, 10c4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX™ platform). The instruction sets and subroutines of content distribution processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to, a smartphone (not shown), a personal digital assistant (not shown), a tablet computer (not shown), laptop computers 28, 30, 32, personal computer 34, a notebook computer (not shown), a server computer (not shown), a gaming console (not shown), and a dedicated network device (not shown). Client electronic devices 28, 30, 32, 34 may each execute an operating system, examples of which may include but are not limited to Microsoft Windows™, Android™, iOS™, Linux™, or a custom operating system.

Users 36, 38, 40, 42 may access content distribution process 10 directly through network 14 or through secondary network 18. Further, content distribution process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, laptop computer 28 and laptop computer 30 are shown wirelessly coupled to network 14 via wireless communication channels 44, 46 (respectively) established between laptop computers 28, 30 (respectively) and cellular network/bridge 48, which is shown directly coupled to network 14. Further, laptop computer 32 is shown wirelessly coupled to network 14 via wireless communication channel 50 established between laptop computer 32 and wireless access point (i.e., WAP) 52, which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between laptop computer 32 and WAP 52. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

System Overview

Figure 2:
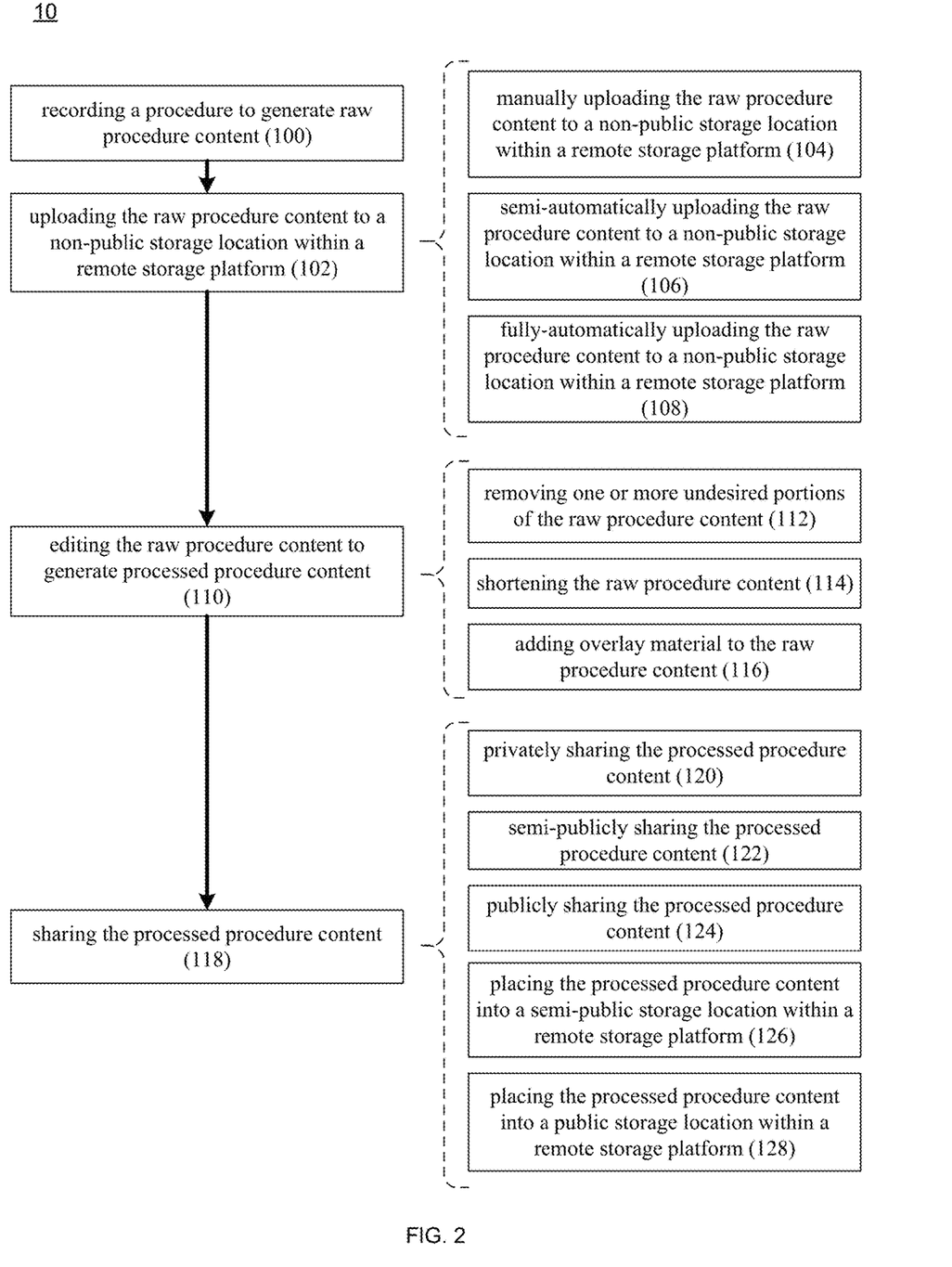
FIG. 2 is a flowchart of the content distribution process of FIG. 1 according to an embodiment of the present disclosure.
Figure 3:
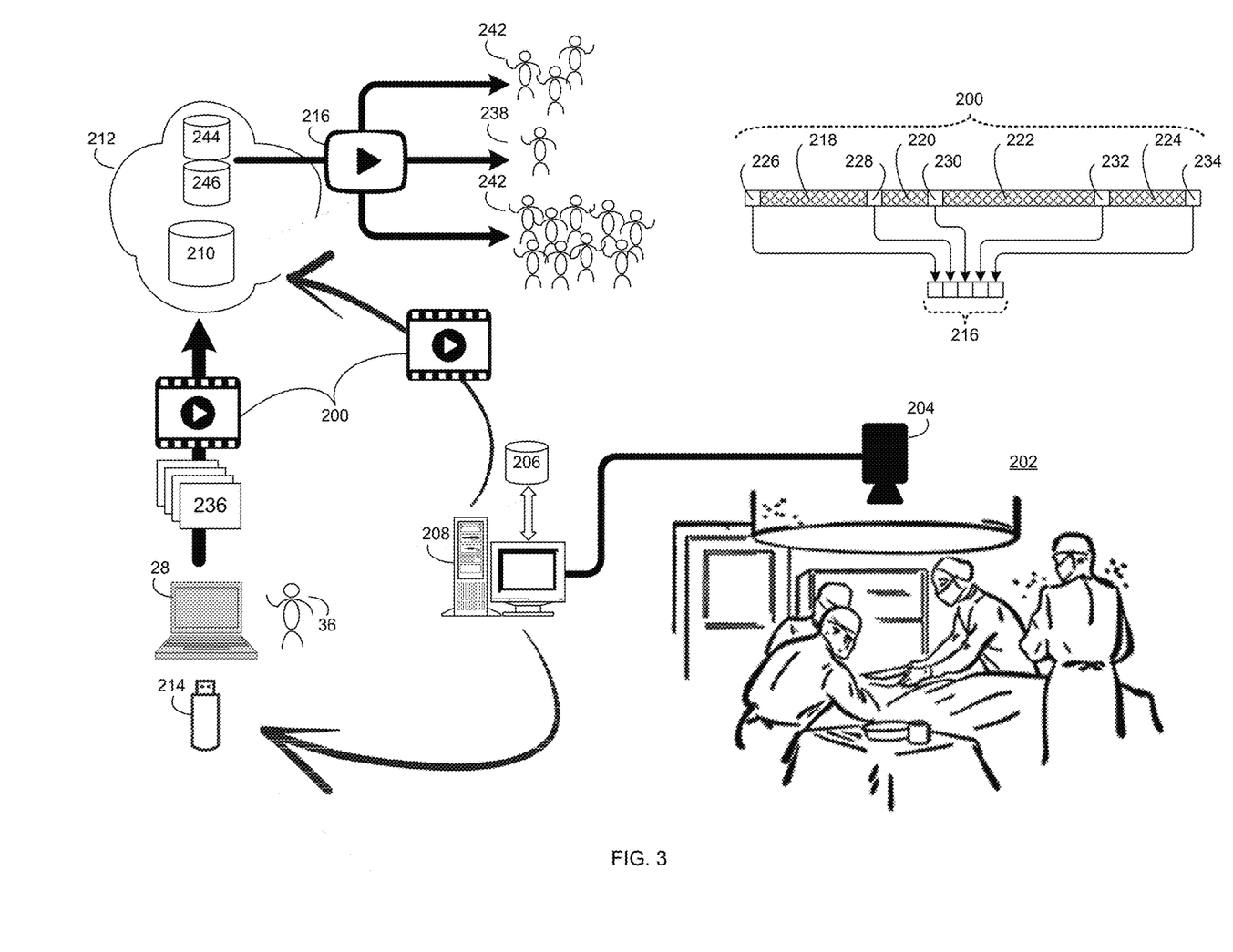
FIG. 3 is a diagrammatic view of a content distribution platform accessible by the content distribution process of FIG. 1 according to an embodiment of the present disclosure.

Referring also to FIGS. 2-3, content distribution process 10 may record 100 a procedure to generate raw procedure content (e.g., raw procedure content 200). An example of such a procedure being recorded may include but is not limited to a medical procedure occurring within a surgical suite (e.g., surgical suite 202). An example of raw procedure content (e.g., raw procedure content 200) may include but is not limited to video-based raw procedure content. For example, a camera (e.g., camera 204) may be installed within surgical suite 202 so that it could record medical procedures that occur within surgical suite 202 at any given time.

For example, while a surgical procedure is being performed within surgical suite 202, camera 204 (e.g., a video camera) may be recording the entire surgical procedure, resulting in the generation of the raw procedure content (e.g., raw procedure content 200) that may be temporarily stored on storage device 206 coupled to computer 208. Camera 204 may be permanently affixed within surgical suite 202 (e.g., ceiling mounted or wall mounted) or temporarily affixed within surgical suite 202 (e.g., tripod mounted or worn by the medical practitioner). Computer 208 may be positioned proximate surgical suite 202 (e.g., within surgical suite 202, next to surgical suite 202 or in the same facility as surgical suite 202).

Content distribution process 10 may upload 102 the raw procedure content (e.g., raw procedure content 200) to a non-public storage location (e.g., non-public storage location 210) within a remote storage platform (e.g., remote storage platform 212). An example of the remote storage platform (e.g., remote storage platform 212) may include but is not limited to a cloud-based remote storage platform.

As is known in the art, cloud storage is a model of computer data storage in which the digital data is stored in logical pools, said to be on "the cloud". The physical storage spans multiple servers (sometimes in multiple locations), and the physical environment is typically owned and managed by a hosting company. These cloud storage providers are responsible for keeping the data available and accessible, and the physical environment secured, protected, and running. People and organizations buy or lease storage capacity from the providers to store user, organization, or application data. Examples of such providers include Microsoft™, Google™ and Amazon™.

When uploading 102 the raw procedure content (e.g., raw procedure content 200) to a non-public storage location (e.g., non-public storage location 210) within a remote storage platform (e.g., remote storage platform 212), content distribution process 10 may manually upload 104 the raw procedure content (e.g., raw procedure content 200) to a non-public storage location (e.g., non-public storage location 210) within a remote storage platform (e.g., remote storage platform 212).

As discussed above, the raw procedure content (e.g., raw procedure content 200) may be temporarily stored on storage device 206 coupled to computer 208. Accordingly and when manually uploading 104 raw procedure content 200 to non-public storage location 210 within remote storage platform 212, user 36 may copy raw procedure content 200 from storage device 206 to e.g., a portable storage device (e.g., USB drive 214) so that user 36 may then copy raw procedure content 200 from e.g., the portable storage device (e.g., USB drive 214) to laptop computer 28. Content distribution process 10 may then enable user 36 to manually upload 104 raw procedure content 200 from laptop computer 28 to non-public storage location 210 within remote storage platform 212.

When uploading 102 the raw procedure content (e.g., raw procedure content 200) to a non-public storage location (e.g., non-public storage location 210) within a remote storage platform (e.g., remote storage platform 212), content distribution process 10 may semi-automatically upload 106 the raw procedure content (e.g., raw procedure content 200) to a non-public storage location (e.g., non-public storage location 210) within a remote storage platform (e.g., remote storage platform 212).

As discussed above, the raw procedure content (e.g., raw procedure content 200) may be temporarily stored on storage device 206 coupled to computer 208. Accordingly and when semi-automatically uploading 106 raw procedure content 200 to non-public storage location 210 within remote storage platform 212, user 36 may log into computer 208 to initiate the semi-automatic upload 106 of raw procedure content 200 from computer 208 to non-public storage location 210 within remote storage platform 212.

When uploading 102 the raw procedure content (e.g., raw procedure content 200) to a non-public storage location (e.g., non-public storage location 210) within a remote storage platform (e.g., remote storage platform 212), content distribution process 10 may fully-automatically upload 108 the raw procedure content (e.g., raw procedure content 200) to a non-public storage location (e.g., non-public storage location 210) within a remote storage platform (e.g., remote storage platform 212).

As discussed above, the raw procedure content (e.g., raw procedure content 200) may be temporarily stored on storage device 206 coupled to computer 208. Accordingly and when fully-automatically uploading 108 raw procedure content 200 to non-public storage location 210 within remote storage platform 212, content distribution process 10 may automatically initiate the fully-automatically upload 108 of raw procedure content 200 from computer 208 to non-public storage location 210 within remote storage platform 212.

Content distribution process 10 may edit 110 the raw procedure content (e.g., raw procedure content 200) to generate processed procedure content (e.g., processed procedure content 216). Generally speaking and as will be discussed below, the raw procedure content (e.g., raw procedure content 200) may be considerably long (e.g., multiple hours for long procedures) and may have large portions of non-interesting material (e.g., prep procedures and closing procedures). Accordingly, content distribution process 10 may be configured to enable user 36 to edit 110 raw procedure content 200 to generate processed procedure content 216. Additionally, content distribution process 10 may be configured to allow the user (e.g., user 36) to add tags (e.g., Surgery Type: Pathology) to the raw procedure content (e.g., raw procedure content 200) so that e.g., the user (e.g., user 36) may search their raw content sometime in the future.

When editing 110 the raw procedure content (e.g., raw procedure content 200) to generate processed procedure content (e.g., processed procedure content 210), content distribution process 10 may remove 112 one or more undesired portions of the raw procedure content (e.g., raw procedure content 200). Assume for this example that raw procedure content 200 includes four undesired portions (e.g., undesired portions 218, 220, 222, 224) that include non-interesting material. Accordingly and when editing 110 the raw procedure content (e.g., raw procedure content 200) to generate processed procedure content (e.g., processed procedure content 210), content distribution process 10 may enable user 36 to remove 112 these undesired portions (e.g., undesired portions 218, 220, 222, 224) of raw procedure content 200. Such an operation may result in the identification of one or more relevant sub-portions (e.g., sub-portions 226, 228, 230, 232, 234) that will be included within processed procedure content 216.

Accordingly and when editing 110 the raw procedure content (e.g., raw procedure content 200) to generate processed procedure content (e.g., processed procedure content 210), content distribution process 10 may shorten 114 the raw procedure content (e.g., raw procedure content 200). As discussed above, raw procedure content 200 may be considerable long (e.g., multiple hours for long procedures) and may have large portions of non-interesting material (e.g., prep procedures and closing procedures). Accordingly and when removing 112 these undesired portions (e.g., undesired portions 218, 220, 222, 224) of raw procedure content 200, this procedure may result in the shortening 114 of raw procedure content 200 (often considerably).

Further and when editing 110 raw procedure content (e.g., raw procedure content 200) to generate processed procedure content (e.g., processed procedure content 210), content distribution process 10 may add 116 overlay material (e.g., overlay material 236) to the raw procedure content (e.g., raw procedure content 200). Examples of such overlay material (e.g., overlay material 236) may include but are not limited to: text-based overlay material, image/video-based overlay material and voice-based overlay material. For example, content distribution process 10 may enable user 36 to:

add 116 text-based overlay material (e.g., overlay material 236) to the raw procedure content (e.g., raw procedure content 200), wherein this text-based overlay material (e.g., overlay material 236) may provide textual information elaborating on the underlying raw procedure content 200;

add 116 image/video-based overlay material (e.g., overlay material 236) to the raw procedure content (e.g., raw procedure content 200), wherein this image/video-based overlay material (e.g., overlay material 236) may provide visual information (e.g., graphical images/forward facing camera) elaborating on the underlying raw procedure content 200; and/or add 116 voice-based overlay material (e.g., overlay material 236) to the raw procedure content (e.g., raw procedure content 200), wherein this voice-based overlay material (e.g., overlay material 236) may provide voiceover information elaborating on the underlying raw procedure content 200;

Once raw procedure content 200 is edited 110 to generate processed procedure content 216, content distribution process 10 may share 118 the processed procedure content (e.g., processed procedure content 210). For example and when sharing 118 the processed procedure content (e.g., processed procedure content 210), content distribution process 10 may:

privately share 120 the processed procedure content (e.g., processed procedure content 210), wherein content distribution process 10 may enable user 36 to privately share 120 the processed procedure content (e.g., processed procedure content 210) with a specific individual (e.g., viewer 238) in a manner similar to a direct message;

semi-publicly share 122 the processed procedure content (e.g., processed procedure content 210), wherein content distribution process 10 may enable user 36 to semi-publicly share 122 the processed procedure content (e.g., processed procedure content 210) with a specific group of individuals (e.g., group 240) in a manner similar to a friend group on a social media platform; and/or publicly share 124 the processed procedure content (e.g., processed procedure content 210), wherein content distribution process 10 may enable user 36 to publicly share 124 the processed procedure content (e.g., processed procedure content 210) with everyone (e.g., everyone 242) in a manner similar to distributing content on the internet without any restrictions.

Accordingly and when sharing 118 the processed procedure content (e.g., processed procedure content 210), content distribution process 10 may:

place 126 the processed procedure content (e.g., processed procedure content 210) into a semi-public storage location (e.g., semi-public storage location 244) within the remote storage platform (e.g., remote storage platform 208) that is accessible only to individuals having the appropriate access rights (e.g., viewer 238 and/or group 240); and/or place 128 the processed procedure content (e.g., processed procedure content 210) into a public storage location (e.g., public storage location 246) within the remote storage platform (e.g., remote storage platform 208) that is accessible to all individuals regardless of access rights (e.g., everyone 242).

Once shared 118, processed procedure content (e.g., processed procedure content 210) may be available to various people (e.g., viewer 238, group 240 and/or everyone 242). Further, content distribution process 10 may enable e.g., user 36 to search for various pieces of content that they shared, wherein this content may be organized in accordance with various pieces of metadata associated with the content. As is known in the art, such metadata may define e.g., the time/date that the processed procedure content (e.g., processed procedure content 210) was shared, the location at which the processed procedure content (e.g., processed procedure content 210) was recorded, the subject matter of the processed procedure content (e.g., processed procedure content 210), etc.

Naturally, any and all sharing of the above-described processed procedure content (e.g., processed procedure content 210) by user 36 must adhere to and be compliant with any & all patient confidentiality rules, laws, regulations and requirements. For example, any & all sharing of such processed procedure content (e.g., processed procedure content 210) must adhere to and be compliant with all HIPAA requirements.

As is known, the Health Insurance Portability and Accountability Act of 1996 (HIPAA or the Kennedy-Kassebaum Act) is a United States Act of Congress enacted by the 104th United States Congress and signed into law by President Bill Clinton on Aug. 21, 1996. It modernized the flow of healthcare information, stipulates how personally identifiable information maintained by the healthcare and healthcare insurance industries should be protected from fraud and theft, and addressed some limitations on healthcare insurance coverage. It generally prohibits healthcare providers and healthcare businesses, called covered entities, from disclosing protected information to anyone other than a patient and the patient's authorized representatives without their consent. With limited exceptions, it does not restrict patients from receiving information about themselves. It does not prohibit patients from voluntarily sharing their health information however they choose, nor does it require confidentiality where a patient discloses medical information to family members, friends, or other individuals not a part of a covered entity.

One or more of the above-described processes and/or procedures may be partially or fully effectuated through the use of machine learning/artificial intelligence.

As is known in the art, machine learning (ML) is a field of inquiry devoted to understanding and building methods that 'learn', that is, methods that leverage data to improve performance on some set of tasks. It is seen as a part of artificial intelligence. Machine learning algorithms build a model based on sample data, known as training data, in order to make predictions or decisions without being explicitly programmed to do so. Machine learning algorithms are used in a wide variety of applications, such as in medicine, email filtering, speech recognition, and computer vision, where it is difficult or unfeasible to develop conventional algorithms to perform the needed tasks.

A subset of machine learning is closely related to computational statistics, which focuses on making predictions using computers, but not all machine learning is statistical learning. The study of mathematical optimization delivers methods, theory and application domains to the field of machine learning. Data mining is a related field of study, focusing on exploratory data analysis through unsupervised learning. Some implementations of machine learning use data and neural networks in a way that mimics the working of a biological brain. In its application across business problems, machine learning is also referred to as predictive analytics.

As is known in the art, a machine learning system or model may generally include an algorithm or combination of algorithms that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As the machine learning system navigates its problem space, the machine learning system is provided feedback that's analogous to rewards, which it tries to maximize. While three examples of machine learning approaches have been provided, it will be appreciated that other machine learning approaches are possible within the scope of the present disclosure.

Video Editor

Figure 4:
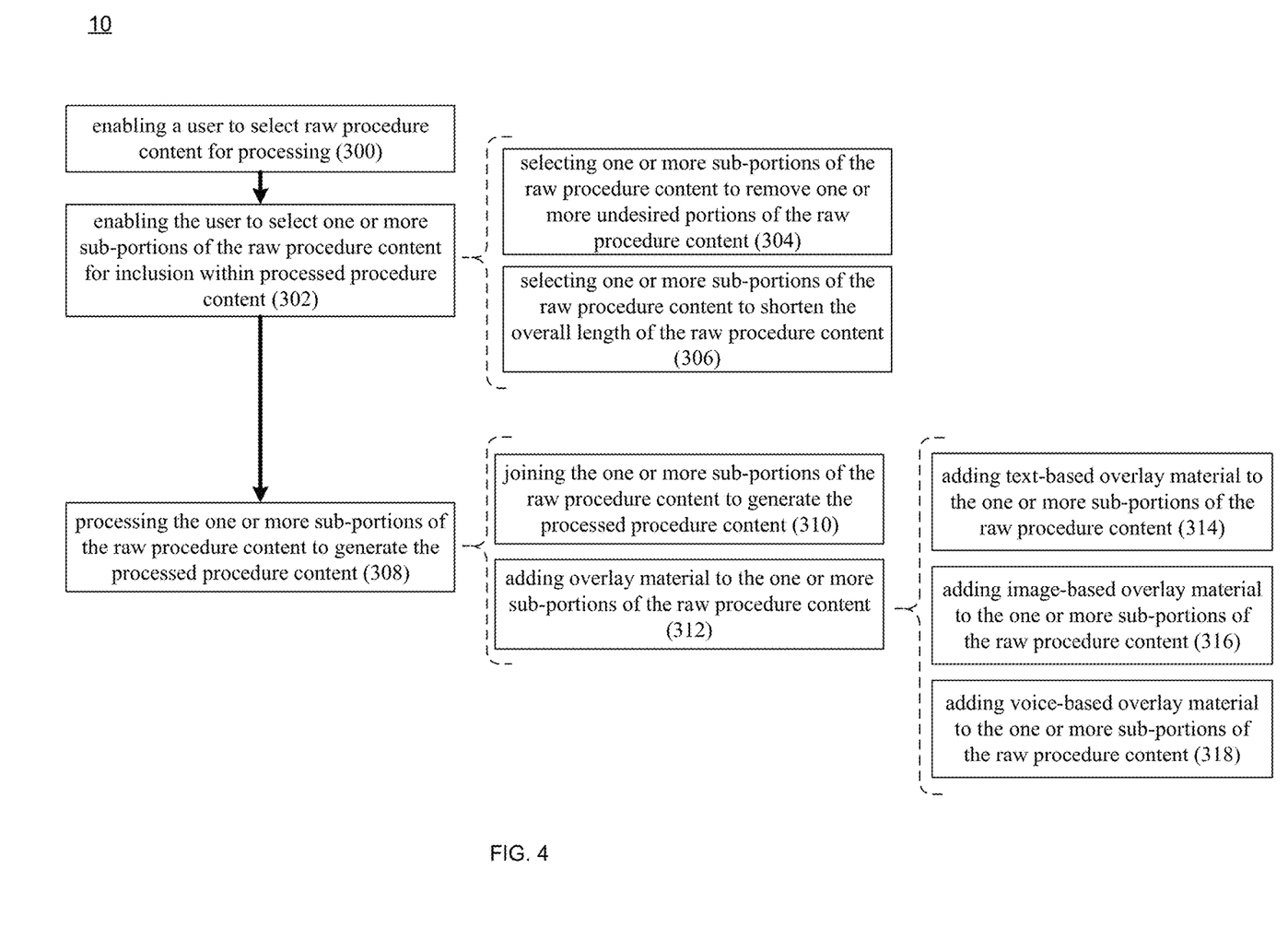
FIG. 4 is another flowchart of the content distribution process of FIG. 1 according to an embodiment of the present disclosure.

Referring also to FIG. 4 and as discussed above, content distribution process 10 may enable 300 a user (e.g., user 36) to select raw procedure content (e.g., raw procedure content 200) for processing. Specifically, once the raw procedure content (e.g., raw procedure content 200) is uploaded 102 to non-public storage location 210 within remote storage platform 212, content distribution process 10 may enable 300 a user (e.g., user 36) to select raw procedure content (e.g., raw procedure content 200) for processing, wherein the selection may be made from the various pieces of raw procedure content available for processing via content distribution process 10.

Once selected 300, content distribution process 10 may enable 302 the user (e.g., user 36) to select one or more sub-portions (e.g., sub-portions 226, 228, 230, 232, 234) of the raw procedure content (e.g., raw procedure content 200) for inclusion within processed procedure content (e.g., processed procedure content 210). Generally speaking, by enabling 302 user 36 to select one or more sub-portions (e.g., sub-portions 226, 228, 230, 232, 234) of the raw procedure content (e.g., raw procedure content 200) for inclusion within processed procedure content (e.g., processed procedure content 210), user 36 does not need to select the undesired portions (e.g., undesired portions 218, 220, 222, 224) of raw procedure content 200 for exclusion from processed procedure content (e.g., processed procedure content 210). As the undesired portions (e.g., undesired portions 218, 220, 222, 224) of raw procedure content 200 are often substantially larger/more frequent than sub-portions (e.g., sub-portions 226, 228, 230, 232, 234) of raw procedure content 200, this process may be considerably easier for the user (e.g., user 36).

When enabling 302 the user (e.g., user 36) to select one or more sub-portions (e.g., sub-portions 226, 228, 230, 232, 234) of the raw procedure content (e.g., raw procedure content 200) for inclusion in processed procedure content (e.g., processed procedure content 210), content distribution process 10 may select 304 one or sub-portions (e.g., sub-portions 226, 228, 230, 232, 234) of the raw procedure content (e.g., raw procedure content 200) to remove one or more undesired portions (e.g., undesired portions 218, 220, 222, 224) of the raw procedure content (e.g., raw procedure content 200). Specifically, by only selecting the sub-portions (e.g., sub-portions 226, 228, 230, 232, 234) that user 36 is interested in, user 36 is also passively selecting the portions that they are not interested in (e.g., undesired portions 218, 220, 222, 224).

When enabling 302 the user (e.g., user 36) to select one or more sub-portions (e.g., sub-portions 226, 228, 230, 232, 234) of the raw procedure content (e.g., raw procedure content 200) for inclusion in processed procedure content (e.g., processed procedure content 210), content distribution process 10 may select 306 one or more sub-portions (e.g., sub-portions 226, 228, 230, 232, 234) of the raw procedure content (e.g., raw procedure content 200) to shorten the overall length of the raw procedure content (e.g., raw procedure content 200) due to e.g., the removal of undesired portions 218, 220, 222, 224).

Once selected 304, 306, content distribution process 10 may process 308 the one or more sub-portions of the raw procedure content (e.g., raw procedure content 200) to generate the processed procedure content (e.g., processed procedure content 210).

For example and when processing 308 the one or more sub-portions (e.g., sub-portions 226, 228, 230, 232, 234) of the raw procedure content (e.g., raw procedure content 200) to generate the processed procedure content (e.g., processed procedure content 210), content distribution process 10 may join 310 the one or more sub-portions (e.g., sub-portions 226, 228, 230, 232, 234) of the raw procedure content (e.g., raw procedure content 200) to generate the processed procedure content (e.g., processed procedure content 210). Content distribution process 10 may enable user 36 to reorder the sub-portions (e.g., sub-portions 226, 228, 230, 232, 234) so that they may be sequenced in whatever order is desirable.

When processing 308 the one or more sub-portions (e.g., sub-portions 226, 228, 230, 232, 234) of the raw procedure content (e.g., raw procedure content 200) to generate the processed procedure content (e.g., processed procedure content 210), content distribution process 10 may add 312 overlay material (e.g., overlay material 236) to the one or more sub-portions (e.g., sub-portions 226, 228, 230, 232, 234) of the raw procedure content (e.g., raw procedure content 200).

As discussed above and when adding 312 overlay material (e.g., overlay material 236) to the one or more sub-portions (e.g., sub-portions 226, 228, 230, 232, 234) of the raw procedure content (e.g., raw procedure content 200), content distribution process 10 may:

add 314 text-based overlay material (e.g., overlay material 236) to the one or more sub-portions (e.g., sub-portions 226, 228, 230, 232, 234) of the raw procedure content (e.g., raw procedure content 200), wherein this text-based overlay material (e.g., overlay material 236) may provide textual information elaborating on the underlying sub-portions (e.g., sub-portions 226, 228, 230, 232, 234);

add 316 image/video-based overlay material (e.g., overlay material 236) to the one or more sub-portions (e.g., sub-portions 226, 228, 230, 232, 234) of the raw procedure content (e.g., raw procedure content 200), wherein this image/video-based overlay material (e.g., overlay material 236) may provide visual information (e.g., graphical images/forward facing camera) elaborating on sub-portions (e.g., sub-portions 226, 228, 230, 232, 234); and/or add 318 voice-based overlay material (e.g., overlay material 236) to the one or more sub-portions (e.g., sub-portions 226, 228, 230, 232, 234) of the raw procedure content (e.g., raw procedure content 200), wherein this voice-based overlay material (e.g., overlay material 236) may provide voiceover information elaborating on sub-portions (e.g., sub-portions 226, 228, 230, 232, 234).

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method executed on a computing device comprising:
    enabling a user to select raw procedure content for processing;
    enabling the user to select one or more sub-portions of the raw procedure content for inclusion within processed procedure content, including:
        receiving a user selection of a general portion of the raw procedure content;
        zooming into the selected general portion of the raw procedure content at a predefined level of granularity; and
        receiving an exact selection of one or more of a start and an end of the sub-portions from the zoomed selected general portion; and
    processing the one or more sub-portions of the raw procedure content to generate the processed procedure content, including joining the one or more sub-portions of the raw procedure content to generate the processed procedure content.

2. The computer-implemented method of claim 1 wherein the raw procedure content includes video-based raw procedure content.

3. The computer-implemented method of claim 1 wherein the raw procedure content concerns a medical procedure.

4. The computer-implemented method of claim 1 wherein the raw procedure content is stored at a non-public storage location within a remote storage platform.

5. The computer-implemented method of claim 4 wherein the remote storage platform includes a cloud-based remote storage platform.

6. The computer-implemented method of claim 1 wherein enabling the user to select one or more sub-portions of the raw procedure content for inclusion in processed procedure content includes:
    selecting one or more sub-portions of the raw procedure content to shorten the overall length of the raw procedure content.

7. The computer-implemented method of claim 1 wherein enabling the user to select one or more sub-portions of the raw procedure content for inclusion in processed procedure content includes:
    selecting one or more sub-portions of the raw procedure content to remove one or more undesired portions of the raw procedure content.

8. The computer-implemented method of claim 1 wherein processing the one or more sub-portions of the raw procedure content to generate the processed procedure content includes:
    adding overlay material to the one or more sub-portions of the raw procedure content.

9. The computer-implemented method of claim 8 wherein adding overlay material to the one or more sub-portions of the raw procedure content includes one or more of:
    adding text-based overlay material to the one or more sub-portions of the raw procedure content;
    adding image/video-based overlay material to the one or more sub-portions of the raw procedure content; and
    adding voice-based overlay material to the one or more sub-portions of the raw procedure content.

10. A computer program product residing on a non-transitory computer readable medium having a plurality of instructions stored thereon which, when executed by a processor, cause the processor to perform operations comprising:
 enabling a user to select raw procedure content for processing;
 enabling the user to select one or more sub-portions of the raw procedure content for inclusion within processed procedure content, including:
  receiving a user selection of a general portion of the raw procedure content;
  zooming into the selected general portion of the raw procedure content at a predefined level of granularity; and
  receiving an exact selection of one or more of a start and an end of the sub-portions from the zoomed selected general portion; and
 processing the one or more sub-portions of the raw procedure content to generate the processed procedure content, including joining the one or more sub-portions of the raw procedure content to generate the processed procedure content.

11. The computer program product of claim 10 wherein the raw procedure content includes video-based raw procedure content.

12. The computer program product of claim 10 wherein the raw procedure content concerns a medical procedure.

13. The computer program product of claim 10 wherein the raw procedure content is stored at a non-public storage location within a remote storage platform.

14. The computer program product of claim 13 wherein the remote storage platform includes a cloud-based remote storage platform.

15. The computer program product of claim 10 wherein enabling the user to select one or more sub-portions of the raw procedure content for inclusion in processed procedure content includes:
 selecting one or more sub-portions of the raw procedure content to shorten the overall length of the raw procedure content.

16. The computer program product of claim 10 wherein enabling the user to select one or more sub-portions of the raw procedure content for inclusion in processed procedure content includes:
 selecting one or more sub-portions of the raw procedure content to remove one or more undesired portions of the raw procedure content.

17. The computer program product of claim 10 wherein processing the one or more sub-portions of the raw procedure content to generate the processed procedure content includes:
 adding overlay material to the one or more sub-portions of the raw procedure content.

18. The computer program product of claim 17 wherein adding overlay material to the one or more sub-portions of the raw procedure content includes one or more of:
 adding text-based overlay material to the one or more sub-portions of the raw procedure content;
 adding image/video-based overlay material to the one or more sub-portions of the raw procedure content; and
 adding voice-based overlay material to the one or more sub-portions of the raw procedure content.

19. A computing system including a processor and memory configured to perform operations comprising:
 enabling a user to select raw procedure content for processing;
 enabling the user to select one or more sub-portions of the raw procedure content for inclusion within processed procedure content, including:
  receiving a user selection of a general portion of the raw procedure content;
  zooming into the selected general portion of the raw procedure content at a predefined level of granularity; and
  receiving an exact selection of one or more of a start and an end of the sub-portions from the zoomed selected general portion; and
 processing the one or more sub-portions of the raw procedure content to generate the processed procedure content, including joining the one or more sub-portions of the raw procedure content to generate the processed procedure content.

20. The computing system of claim 19 wherein the raw procedure content includes video-based raw procedure content.

21. The computing system of claim 19 wherein the raw procedure content concerns a medical procedure.

22. The computing system of claim 19 wherein the raw procedure content is stored at a non-public storage location within a remote storage platform.

23. The computing system of claim 22 wherein the remote storage platform includes a cloud-based remote storage platform.

24. The computing system of claim 19 wherein enabling the user to select one or more sub-portions of the raw procedure content for inclusion in processed procedure content includes:
 selecting one or more sub-portions of the raw procedure content to shorten the overall length of the raw procedure content.

25. The computing system of claim 19 wherein enabling the user to select one or more sub-portions of the raw procedure content for inclusion in processed procedure content includes:
 selecting one or more sub-portions of the raw procedure content to remove one or more undesired portions of the raw procedure content.

26. The computing system of claim 19 wherein processing the one or more sub-portions of the raw procedure content to generate the processed procedure content includes:
 adding overlay material to the one or more sub-portions of the raw procedure content.

27. The computing system of claim 26 wherein adding overlay material to the one or more sub-portions of the raw procedure content includes one or more of:
 adding text-based overlay material to the one or more sub-portions of the raw procedure content;
 adding image/video-based overlay material to the one or more sub-portions of the raw procedure content; and
 adding voice-based overlay material to the one or more sub-portions of the raw procedure content.

* * * * *